United States Patent
Lundgren

[11] Patent Number: 6,083,175
[45] Date of Patent: Jul. 4, 2000

[54] METHOD AND APPARATUS FOR COLLECTING FRAGMENTS OF BONE TISSUE

[75] Inventor: Dan Lundgren, Howas, Sweden

[73] Assignee: Bladhs Medical AB, Bredarvd, Sweden

[21] Appl. No.: 08/819,403

[22] Filed: Mar. 17, 1997

Related U.S. Application Data

[63] Continuation of application No. PCT/SE95/01065, Sep. 20, 1995.

[30] Foreign Application Priority Data

Sep. 20, 1994 [SE] Sweden ................................. 9403183

[51] Int. Cl.⁷ .................................................... A61B 10/00
[52] U.S. Cl. ............................ 600/562; 600/573; 433/90
[58] Field of Search ..................................... 600/562, 563, 600/573; 433/89, 90, 91, 92, 215

[56] References Cited

U.S. PATENT DOCUMENTS

| | | | |
|---|---|---|---|
| 3,623,607 | 11/1971 | Loos ........................................ | 210/106 |
| 3,785,380 | 1/1974 | Brumfield ............................... | 128/276 |
| 3,863,624 | 2/1975 | Gram ....................................... | 128/2 B |
| 3,890,712 | 6/1975 | Lopez ..................................... | 32/33 |
| 4,018,686 | 4/1977 | Shufflebarger et al. ................ | 210/448 |
| 4,083,706 | 4/1978 | Wiley ..................................... | 55/385 R |
| 4,468,217 | 8/1984 | Kuzmick et al. ....................... | 604/48 |
| 4,886,492 | 12/1989 | Brooke ................................... | 604/49 |
| 5,114,240 | 5/1992 | Kindt-Larsen et al. ................ | 366/129 |
| 5,192,439 | 3/1993 | Roth et al. .............................. | 210/485 |
| 5,494,044 | 2/1996 | Sundberg ................................ | 128/749 |
| 5,830,359 | 11/1998 | Knight et al. .......................... | 210/651 |

FOREIGN PATENT DOCUMENTS

| | | |
|---|---|---|
| 0 284 322 | 9/1988 | European Pat. Off. . |
| 5-137736 | 6/1993 | Japan . |

*Primary Examiner*—Cary O'Connor
*Assistant Examiner*—Charles Marmar, II
*Attorney, Agent, or Firm*—Merchant & Gould P.C.

[57] ABSTRACT

Bone tissue fragments are collected from liquid fluid being evacuated by suction from a surgical operation in bone tissue. Liquid is allowed to pass into a cylindrical sieve through one open end thereof and through the sieve wall from the inside to the outside thereof. Bone tissue fragments are collected on the inside surface of the sieve and are scrapped off and deposited outside the sieve.

6 Claims, 1 Drawing Sheet

METHOD AND APPARATUS FOR COLLECTING FRAGMENTS OF BONE TISSUE

This is a continuation of PCT/SE95/01065 application filed Sep. 20, 1995.

FIELD OF THE INVENTION

The invention relates to an apparatus for collecting bone tissue fragments from liquids recovered during surgical operations, as well as to a method of collecting bone tissue fragments.

BACKGROUND OF THE INVENTION

Many surgical operations are carried out in bone tissue. An example includes those operations conducted within the oral cavity for the purpose of fixing dental problems such as crowns, bridges and prosthesis in toothless regions of the jaw. These operations can include drilling holes in the jaw bone to secure titanium screws that are used as anchoring elements. The bone tissue fragments generated during drilling can be used for filling bone cavities within the jaw that were caused by proceeding pathological processes.

An aspirator can be used to remove blood from the operative site. The bone tissue fragments created during the operation (such as drilling) are entrained within the liquid flow and will be lost if they are not separated from the liquid flow and collected. Accordingly, a need remains for a simple way for collecting bone tissue fragments.

SUMMARY OF THE INVENTION

Accordingly, the invention is found in a method for collecting bone tissue fragments from liquid evacuated during a surgical operation within bone tissue. The liquid evacuated by suction is passed into a cylindrical sieve through an open end. The liquid passes through the sieve wall from an inside surface to an outside surface. An end wall which is displaceably disposed at the opposite end of the sieve is then moved axially through the cylindrical sieve so that bone tissue fragments collected on the inside surface of the sieve are scraped off from the inner surface and are deposited outside the sieve from the open end of the sieve.

The invention is also found in a device for collecting bone tissue fragments during surgical operations within bone tissue. The device is cylindrical, with an inlet at one end and an outlet at the other end. The cylindrical device is connected to a suction conduit and there is a cylindrical sieve provided within the device. A space is provided between the outer curved surface of the sieve and the inner curved surface of the cylinder. An open end of the sieve communicates with the inlet of the cylinder and the space communicates with the outlet of the cylinder. The other end of the sieve has an end wall that can be displaced axially through the sieve as a piston.

DETAILED DESCRIPTION

Figure 1:
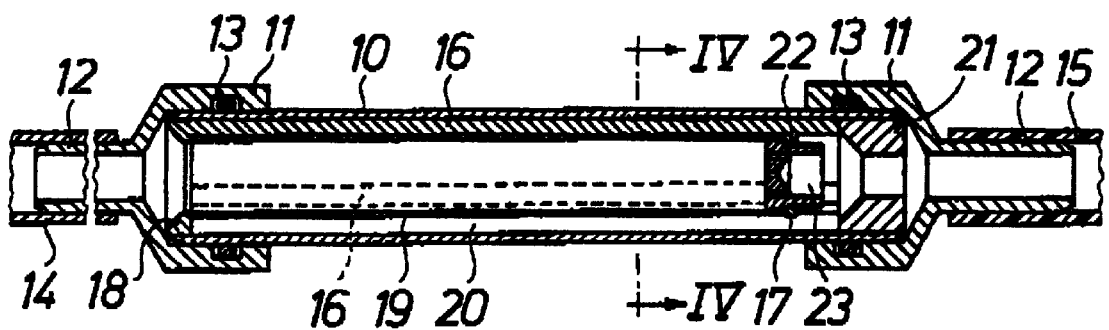
FIG. 1 is an axial cross-sectional view of a device for evacuating liquid by suction and removing bone fragments from the liquid according to the invention.

The device according to the invention comprises a cylinder 10 open at each end. A cover 11 is pushed onto the cylinder 10 at each open end, forming a connection piece 12 and being sealed against the outside surface of the cylinder 10 with an O-ring 13. An aspirator nozzle 14 (seen in fragmentary detail only) is connected to one of the connection pieces (being the left one in FIG. 1). A suction hose 15 is connected to the other connection piece (the right side in FIG. 1) and is also connected to an aspirator (not shown). The left connection piece and aspirator nozzle 14 form an inlet of the cylinder 10 while the right connection piece and suction hose 15 form an outlet of the cylinder 10.

Figure 4:
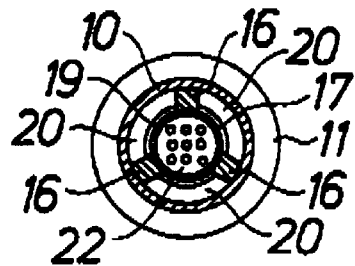
FIG. 4 is a cross-sectional view along line 4—4 of FIG. 1.

A cage comprising three straight bars 16 that extend in parallel and are equally spaced circumferentially, and two rings 17 and 18 that are integral with and interconnect the straight bars, fits detachably in the cylinder 10. The cage receives a cylindrical sieve 19. The cage serves to keep the outside curved surface of the sieve 19 spaced apart from the inside curved surface of the cylinder 10. As a result, the axially extending spaces 20 (as seen in FIG. 4) are maintained. These spaces 20 are separated from the inlet of the cylinder 10 via ring 18, but communicate with the outlet of the cylinder 10 through an annular plug 21 that is fixed in the cylinder 10.

At the end of the sieve adjacent the outlet of the cylinder 10, an end wall 22 is provided that has a thicker portion that fits against the inside surface of the sieve 19 and a narrower portion that forms a hollow stud 23 that fits displaceably in ring 17 when the wall is in the end position as shown in FIG. 1. End wall 22 is axially displaceable along the inside surface of the sieve 19. In the embodiment shown, the end wall 22 is perforated. If the end wall 22 is perforated, it is preferable that the apertures within end wall 22 be smaller than the apertures of sieve 19. Perforations in end wall 22 are not necessary, however. Preferably, the device shown in FIG. 1 is made entirely of plastic and is disposable.

During use, the device is preferably connected in a suction conduit between the aspirator nozzle 14 and the suction hose 15. Low pressure or vacuum is maintained within the suction conduit. If used while drilling occurs in the jaw bone, rinse fluid and blood will be sucked into the sieve 19 via the inlet of the cylinder 10 and will pass through the wall of the sieve 19 into spaces 20 and will then continue to the outlet. Some flow will pass directly to the outlet through perforated end wall 22. The low pressure or vacuum will hold the end wall in the position seen in the Figures as the thicker portion can not pass through ring 17. If the liquid contains coagulated blood or bone tissue fragments, the perforations within end wall 22 will quickly become clogged and the solid particles within the liquid will accumulate on the inside surface of the sieve 19. However, the perforations within end wall 22 provide for a direct continuous flow as long as there are no solid particles to recover.

Figure 2:
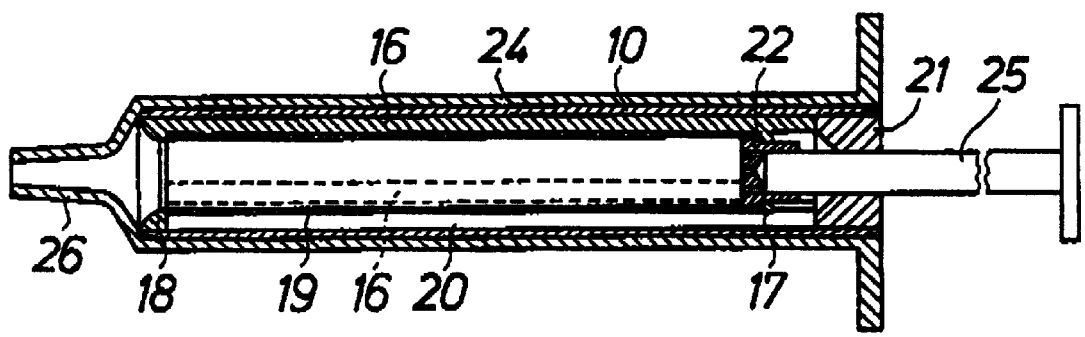
FIG. 2 is a view of the device of FIG. 1, shown in use.
Figure 3:
FIG. 3 is an end view of the axially displaceable end wall in the sieve.

In order to recover the material collected in the sieve 19, cylinder 10 is disconnected from end pieces or hoods 11 and is placed within the cylinder 24 of an ordinary syringe as seen in FIG. 2. A piston rod 24 is then connected to the end wall 22 by inserting the piston rod 24 into stud 23. The end wall 22 is then displaced by moving the piston rod 24 axially through the cylindrical sieve 19, thereby scraping the collected material off from the inside surface of the sieve wall. The material is deposited through connection piece 26 of the cylinder, where the connection piece 26 can be constructed as a Luer connection for connecting a suitable mouth piece to the syringe cylinder.

However, it is not necessary to move cylinder 10 to a syringe for deposition. Instead, it is possible to connect the piston rod to the end wall through the right connection piece 12 (as seen in FIG. 1) and to deposit the material through the left connection piece 12 (of FIG. 1). It may be easier or more comfortable, however, to use a syringe for deposition.

I claim:

1. A device for collecting bone tissue fragments from a liquid fluid flow at a surgical operation in bone tissue, the device comprising:

a tube having axially aligned inlet and outlet sockets at either end of the tube for connection into a suction conduit;

a cylindrical sieve in the tube, a space being provided between an outside curved surface of the sieve and an inside curved surface of the tube, wherein the space is in communication with the outlet socket of the tube;

a piston displaceably received within the sieve, the piston engaging the inside curved surface of the tube, wherein the piston forms an end wall in the sieve at the outlet socket thereof; and a piston rod insertable into the tube through the outlet socket to engage the piston for manual axial displacement through the sieve for deposition of the bone fragments, trapped by the sieve, through the inlet socket of the tube.

2. The device of claim 1, wherein the piston comprises a hollow stud for connection with the piston rod.

3. The device of claim 1, wherein the inlet socket and outlet socket each comprise a cover at the respective ends of the tube, the inlet socket and the outlet socket suitable for connection of an aspirator nozzle and a suction hose, respectively.

4. The device of claim 1, wherein the cylindrical sieve comprises a plurality of apertures and the piston is perforated with apertures that are narrower than the sieve apertures.

5. The device of claim 1, further comprising a cage that comprises axially extending bars serving as spacers between the sieve and the tube, wherein the sieve fits within the cage.

6. A method for collecting bone tissue fragments from a liquid fluid flow at a surgical operation in bone tissue, the method comprising the steps of:

evacuating liquid fluid by suction from a surgical site;

passing the evacuated liquid fluid through a cylindrical sieve through a first opening thereof and through a wall of the sieve from an inside surface to an outside surface, wherein the bone tissue fragments are trapped on the inside surface of the sieve;

inserting a piston rod through a second open end of the cylindrical sieve to engage a piston therein;

manually displacing the piston rod axially through the cylindrical sieve to scrape bone tissue fragments from the inside surface of the sieve with the piston; and depositing the scraped off bone tissue fragments outside the cylindrical sieve through the first open end.

\* \* \* \* \*